United States Patent [19]

Heinemann et al.

[11] Patent Number: 4,826,849
[45] Date of Patent: May 2, 1989

[54] CHLORO-1,2,4-OXADIAZOLES

[75] Inventors: Ulrich Heinemann; Wilhelm Brandes, both of Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 117,273

[22] Filed: Nov. 5, 1987

[30] Foreign Application Priority Data

Nov. 25, 1986 [DE] Fed. Rep. of Germany ....... 3640153

[51] Int. Cl.$^4$ .................. C07D 271/06; A01N 43/82
[52] U.S. Cl. .................................... 514/269; 514/309; 514/312; 514/340; 514/364; 544/219; 544/316; 544/319; 546/135; 546/141; 546/277; 548/132
[58] Field of Search ............... 548/132; 546/277, 135, 546/141; 544/316, 319, 219; 514/364, 340, 309, 312, 269

[56] References Cited

FOREIGN PATENT DOCUMENTS

| 3030661 | 4/1982 | Fed. Rep. of Germany ...... 548/132 |
| 3445205 | 6/1986 | Fed. Rep. of Germany . |
| 222770 | 5/1985 | German Democratic Rep. .................................... 548/132 |
| 0185983 | 2/1986 | United Kingdom ................ 548/132 |

Primary Examiner—Robert Gerstl
Attorney, Agent, or Firm—Sprung Horn Kramer & Woods

[57] ABSTRACT

Fungicidally and bactericidally active 3-chloro-1,2,4-oxadiazoles of the formula

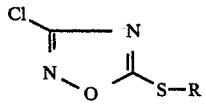

in which R represents optionally substituted aryl or represents optionally substituted heteroaryl.

8 Claims, No Drawings

CHLORO-1,2,4-OXADIAZOLES

The invention relates to new 3-chloro-1,2,4-oxadiazoles, a process for their preparation and their use as agents for combating pests.

It is already known that certain 3-chloro-1,2,4-oxadiazoles, such as, for example, N-(3-chloro-1,2,4-oxadiazol-5-yl)-N'-(4-chlorophenyl)-urea, have fungicidal properties (see U.S. Pat. No. 4,642,312).

However, the activity of these already known compounds is not completely satisfactory in all fields of use, especially when low amounts are applied and in the case of low concentrations.

New 3-chloro-1,2,4-oxadiazoles of the general formula (I)

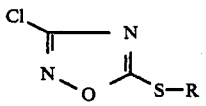
(I)

in which R represents optionally substituted aryl or represents optionally substituted heteroaryl, have been found.

It has furthermore been found that the new 3-chloro-1,2,4-oxadiazoles of the general formula (I)

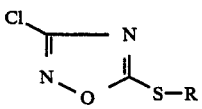
(I)

in which R represents optionally substituted aryl or represents optionally substituted heteroaryl, are obtained by a process in which 3,5-dichloro-1,2,4-oxadiazole of the formula (II)

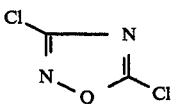
(II)

is reacted with thiols of the general formula (III)

  HS—R    (III)

in which R has the abovementioned meaning, if appropriate in the presence of a diluent and if appropriate in the presence of an acid-binding agent.

Finally, it has been found that the new 3-chloro-1,2,4-oxadiazoles of the formula (I) have an action against pests.

Surprisingly, the 3-chloro-1,2,4-oxadiazoles of the formula (I) according to the invention inter alia exhibit a considerably better fungicidal activity than the 3-chloro-1,2,4-oxadiazoles known from the prior art, such as, for example, N-(3-chloro-1,2,4-oxadiazol-5-yl)-N'-(4-chlorophenyl)-urea, these being closely related compounds chemically and from the point of view of their action.

Formula (I) provides a general definition of the 3-chloro-1,2,4-oxadiazoles according to the invention. Preferred compounds of the formula (I) are those in which R represents aryl which has 6 to 10 carbon atoms and is optionally monosubstituted or polysubstituted by identical or different substituents, or represents 5- to 7-membered heteroaryl which has 1 to 4 optionally identical or different hetero atoms, in particular nitrogen, oxygen and/or sulphur, and is optionally monosubstituted or polysubstituted by identical or different substituents and/or benzo-fused, possible substituents in each case being: halogen, cyano, nitro, in each case straight-chain or branched alkyl, alkoxy, alkylthio, halogenoalkyl, halogenoalkoxy and halogenoalkylthio with in each case 1 to 6 carbon atoms and, where appropriate, 1 to 9 identical or different halogen atoms, hydroxycarbonyl, aminocarbonyl, straight-chain or branched alkoxycarbonyl with 1 to 5 carbon atoms, aryloxy and arylthio with in each case 6 to 10 carbon atoms, in each case straight-chain or branched dialkylamino and alkylcarbonylamino with in each case 1 to 4 carbon atoms in the individual alkyl parts and a 5- or 6-member ring heterocyclic radical which has 1 to 4 optionally identical or different hetero atoms, in particular nitrogen, oxygen and/or sulphur, and is optionally monosubstituted or polysubstituted by identical or different substituents from the group comprising lower alkyl and/or halogen.

Particularly preferred compounds of the formula (I) are those in which R represents phenyl which is optionally mono-, di- or trisubstituted by identical or different substituents, possible substituents being: fluorine, chlorine, bromine, cyano, nitro, methyl, ethyl, n- or i-propyl, n-, i-, s- or t-butyl, n- or i-pentyl, methoxy, ethoxy, n- or i-propoxy, methylthio, ethylthio, n- or i-propylthio, trifluoromethyl, trichloromethyl, tribromomethyl, trifluoromethoxy, trifluoromethylthio, hydroxycarbonyl, aminocarbonyl, methoxycarbonyl, ethoxycarbonyl, phenoxy, phenylthio, dimethylamino, diethylamino, methylcarbonylamino, ethylcarbonylamino and a 5-member ring or 6-member ring heterocyclic radical which has 1 to 4 optionally identical or different hetero atoms, in particular nitrogen, oxygen or sulphur, and is optionally mono- or disubstituted by identical or different substituents from the group comprising chlorine, bromine, methyl and/or ethyl; or represents α-naphthyl or β-naphthyl, in each case optionally mono-, di- or trisubstituted by identical or different substituents, possible substituents being: fluorine, chlorine, bromine, nitro, methyl, ethyl, n- or i-propyl, n-, i-, s- or t-butyl, methoxy, ethoxy, methylthio and trifluoromethyl; or represents 2-pyridyl, 4-pyridyl, 2-pyrimidyl, 4-pyrimidyl, s-triazinyl, 2-quinolyl or 1-isoquinolyl, in each case optionally mono-, di- or trisubstituted by identical or different substituents, possible substituents in each case being: fluorine, chlorine, bromine, cyano, nitro, methyl, ethyl, n- or i-propyl, n-, i-, s- or t-butyl, n- or i-pentyl, methoxy, ethoxy, methylthio, trifluoromethyl, trichloromethyl, tribromomethyl, trifluoromethoxy, trifluoromethylthio, hydroxycarbonyl, aminocarbonyl, methoxycarbonyl, ethoxycarbonyl, dimethylamino, methylcarbonylamino or ethylcarbonylamino.

The following 3-chloro-1,2,4-oxadiazoles of the general formula (I) may be mentioned specifically, in addition to the compounds mentioned in the preparation examples:

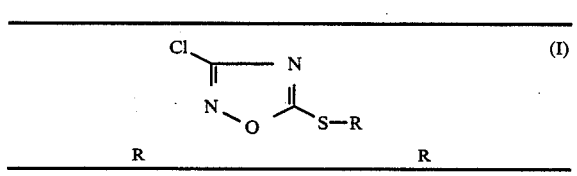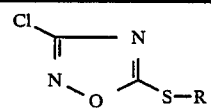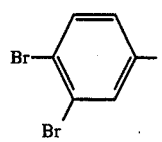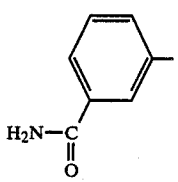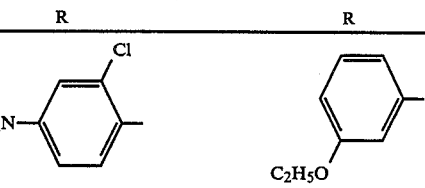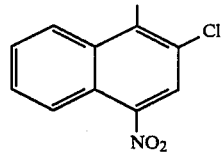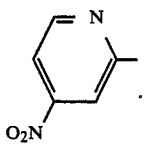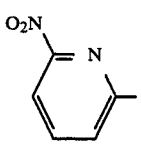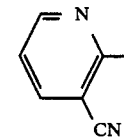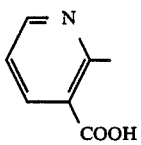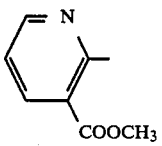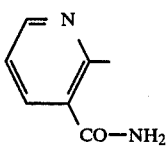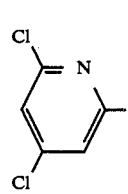

-continued

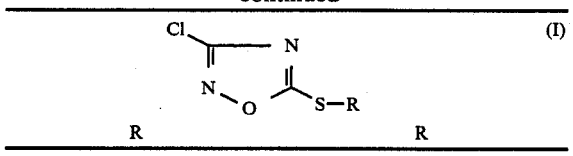

| R | R |
|---|---|
| 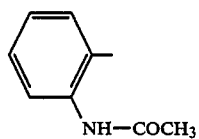 | 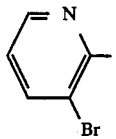 |
| 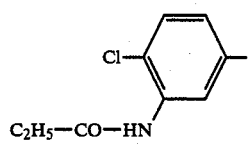 | 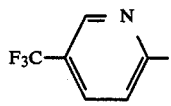 |
| 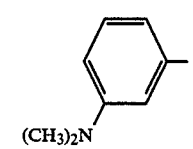 | 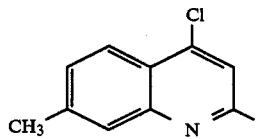 |
| 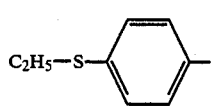 | 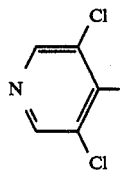 |
| 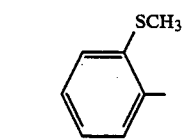 | 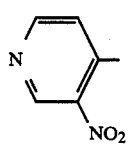 |
| 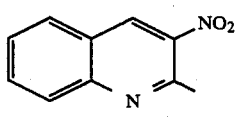 | 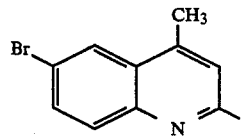 |
| 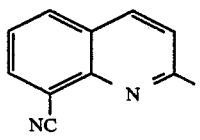 | 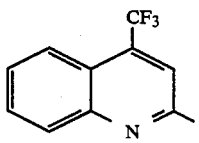 |
| 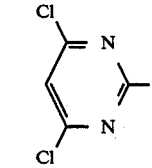 | 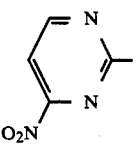 |
| 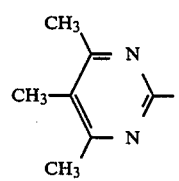 | 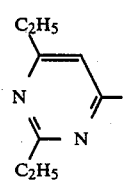 |

-continued

| R | R |
|---|---|
| | 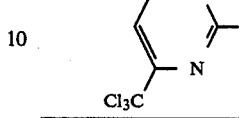 |

If, for example, 3,5-dichloro-1,2,4-oxadiazole and 3-nitro-2-mercaptopyridine are used as starting substances, the course of the reaction in the process according to the invention can be represented by the following equation:

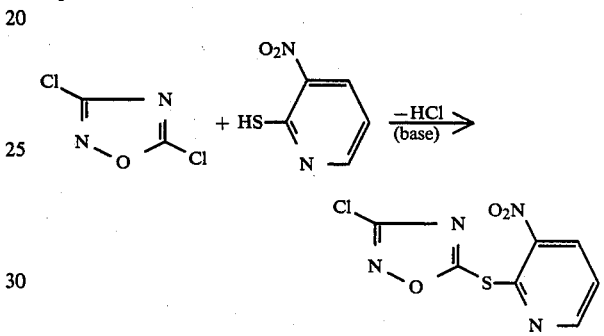

The 3,5-dichloro-1,2,4-oxadiazole of the formula (II) required as the starting substance for carrying out the process according to the invention is known (see U.S. Pat. No. 4,642,312).

Formula (III) provides a general definition of the thiols furthermore required as starting substances for carrying out the process according to the invention. In this formula (III), R represents those radicals which have already been mentioned for this substituent in connection with the description of the substances of the formula (I) according to the invention.

The thiols of the formula (III) are generally known compounds of organic chemistry or are obtainable analogously to known compounds with the aid of generally known processes.

Possible diluents for carrying out the process according to the invention are inert organic solvents.

These include, in particular, aliphatic, alicyclic or aromatic, optionally halogenated hydrocarbons, such as, for example, benzine, benzene, toluene, xylene, chlorobenzene, petroleum ether, hexane cyclohexane, methylene chloride, chloroform and carbon tetrachloride; ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate, or sulphoxides, such as dimethylsulphoxide.

If appropriate, the process according to the invention can be carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a substantial range in carrying out the process according to the invention. The reaction is in general carried out at temperatures between $-20°$ C. and $+140°$ C., preferably at temperatures between $+20°$ C. and $+70°$ C.

For carrying out the process according to the invention, in general 0.7 to 1.0 mol, preferably equimolar amounts, of thiol of the formula (III) and 1.0 to 1.5 mols, preferably equimolar amounts, of base are employed per mol of 3,5-dichloro-1,2,4-oxadiazole of the formula (II). The reaction is carried out and the reaction products of the formula (I) are worked up and isolated by generally customary processes.

The active compounds according to the invention have a powerful action against pests and can be used in practice for combating undesirable harmful organisms. The active compounds are suitable, for example, for use as plant protection agents, in particular as fungicides and bactericides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can thereby be used with particularly good success for combating fungal diseases in fruit and cereal growing, such as, for example, against the apple scab causative organism (*Venturia inaequalis*) or against the rice spot disease causative organism (*Pyricularia oryzae*). Because of their systemic action, they are also particularly suitable as seed dressing agents. The broad fungicidal activity of the compounds moreover also manifests itself under in vitro tests.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulation used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants ca also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

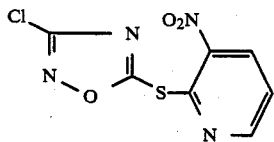

7.0 g (0.05 mol) of 3,5-dichloro-1,2,4-oxadiazole in 25 ml of anhydrous acetonitrile are added dropwise to 7.8 g (0.05 mol) of 3-nitro-2-mercaptopyridine (compare Int. J. Pept. Prot. Res. 16, 392 (180)) and 6.9 g (0.05 mol) of potassium carbonate in 100 ml of anhydrous acetonitrile at room temperature, with stirring. When the addition has ended, the mixture is heated to the reflux temperature for 1 hour, and after cooling, 300 ml of water are added, the mixture is extracted three times with 200 ml of methylene chloride each time and the combined organic phases are washed with 200 ml of water, dried over sodium sulphate and concentrated in vacuo. The residue crystallizes from diisopropyl ether.

10.2 g (79% of theory) of 3-chloro-5-(3-nitro-2-pyridylthio)-1,2,4-oxadiazole of melting point 84° C. are obtained.

The following 3-chloro-1,2,4-oxadiazoles of the general formula (I) are obtained in a corresponding manner and in accordance with the general statements on the preparation:

$$\underset{\text{(I)}}{\text{Cl-C(=N-O-)-C(=N)-S-R}}$$

| Example No. | R | Melting point [°C.] |
|---|---|---|
| 2 | 4-chlorophenyl | oil (boiling point 125° C.–127° C./1.3 bar) |
| 3 | phenyl | oil (boiling point 109° C.–111° C./1.5 mbar) |
| 4 | 4-bromophenyl | 47–48 |
| 5 | 3-(3-chloro-1,2,4-oxadiazol-5-ylthio)phenyl | 64–65 |
| 6 | 4-(1H-tetrazol-1-yl)phenyl | 121–123 |
| 7 | 2-methoxyphenyl | 44–46 |
| 8 | 4-(acetylamino)phenyl | 167–168 |
| 9 | 3,4-dimethylphenyl | 53–54 |

-continued

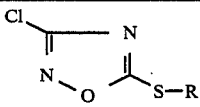  (I)

| Example No. | R | Melting point [°C.] |
|---|---|---|
| 10 | 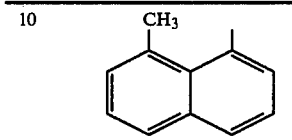 | 142–143 |
| 11 | 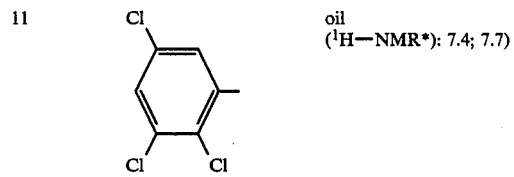 | oil (¹H—NMR*): 7.4; 7.7) |
| 12 | 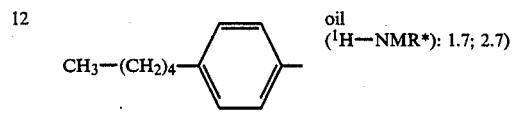 | oil (¹H—NMR*): 1.7; 2.7) |
| 13 | 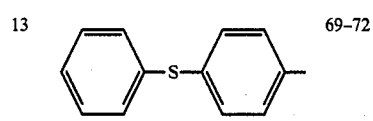 | 69–72 |
| 14 | 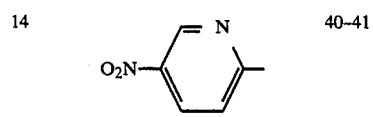 | 40–41 |
| 15 | 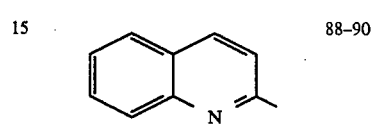 | 88–90 |
| 16 | 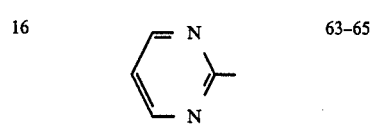 | 63–65 |
| 17 | 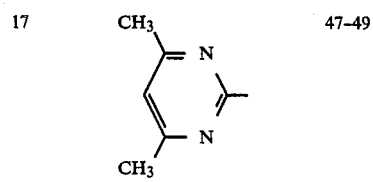 | 47–49 |
| 18 | 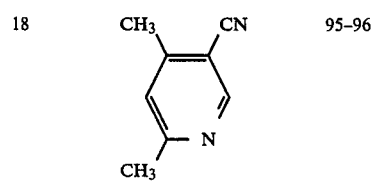 | 95–96 |
| 19 | 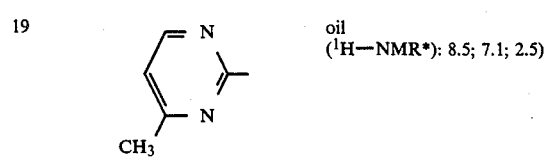 | oil (¹H—NMR*): 8.5; 7.1; 2.5) |

-continued

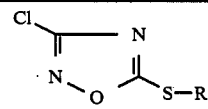  (I)

| Example No. | R | Melting point [°C.] |
|---|---|---|
| 20 | 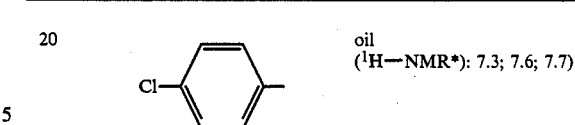 | oil (¹H—NMR*): 7.3; 7.6; 7.7) |
| 21 | 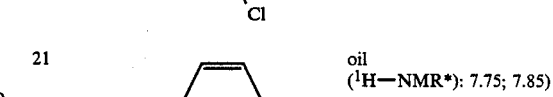 | oil (¹H—NMR*): 7.75; 7.85) |
| 22 | 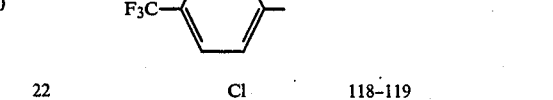 | 118–119 |
| 23 | 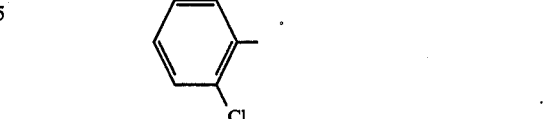 | oil (¹H—NMR*): 1.4; 1.85; 8.6) |
| 24 | 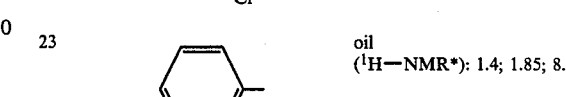 | Oil |
| 25 | 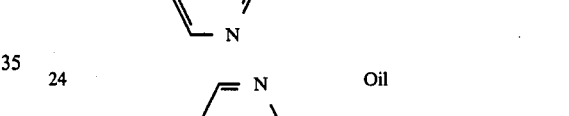 | Oil |
| 26 | 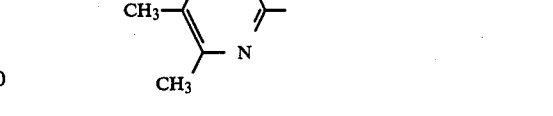 | Oil |
| 27 | 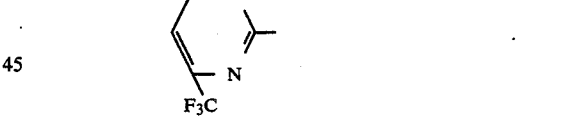 | Oil |

*The ¹H—NMR spectra were recorded in CDCl₃ with tetramethylsilane (TMS) as the internal standard. The chemical shift is stated as δ value in ppm.

USE EXAMPLES

The compound shown below was employed as the comparison substance in the following use examples:

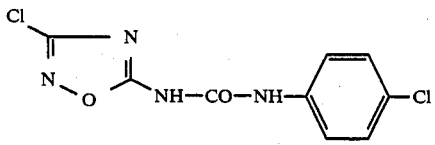

N-(3-Chloro-1,2,4-oxadiazol-5-yl)-N'-(4-chlorophenyl-)urea (known from U.S. Pat. No. 4,642,312).

EXAMPLE A

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plant are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to Preparation Examples 5, 6, 8, 13 and 15.

It will be understood that the specification and examples are illustrative but not limitative of the present invention and that other embodiments within the spirit and scope of the invention will suggest themselves to those skilled in the art.

We claim:

1. A 3-chloro-1,2,4-oxadiazole of the formula

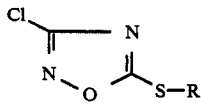

in which R represents phenyl which is optionally mono-, di- or trisubstituted by identical or different substituents selected from the group consisting of fluorine, chlorine, bromine, cyano, nitro, methyl, ethyl, n- or i-propyl, n-, i-, s- or t-butyl, n- or i-pentyl, methoxy, ethoxy, n- or i-propoxy, methylthio, ethylthio, n- or i-propylthio, trifluoromethyl, trichloromethyl, tribromomethyl, trifluoromethoxy, trifluoromethylthio, hydroxycarbonyl, aminocarbonyl, methoxycarbonyl, ethoxycarbonyl, phenoxy, phenylthio, 3-chloro-2,4-oxadiazol-5-yl-thio, dimethylamino, diethylamino, methylcarbonylamino, ethylcarbonylamino and a 5-membered ring or 6-membered ring heterocyclic radical which has 1 to 4 optionally identical or different nitrogen, oxygen or sulphur hetero atoms, and is optionally mono- or disubstituted by identical or different substituents from the group consisting of chlorine, bromine, methyl and/or ethyl; or represents α-naphthyl or β-naphthyl, in each case optionally mono-, di- or trisubstituted by identical or different substituents selected from the group consisting of fluorine, chlorine, bromine, nitro, methyl, ethyl, n- or i-propyl, n-, i-, s- or t-butyl, methoxy, ethoxy, methylthio and trifluoromethyl; or represents 2-pyridyl, 4-pyridyl, 2-pyrimidyl, 4-pyrimidyl, s-triazinyl, 2-quinolyl or 1-isoquinolyl, in each case optionally mono-, di- or trisubstituted by identical or different substituents selected from the group consisting of fluorine, chlorine, bromine, cyano, nitro, methyl, ethyl, n- or i-propyl, n-, i-, s- or t-butyl, n- or i-pentyl, methoxy, ethoxy, methylthio, trifluoromethyl, trichloromethyl, tribromomethyl, trifluoromethoxy, trifluoromethylthio, hydroxycarbonyl, aminocarbonyl, methoxycarbonyl, ethoxycarbonyl, dimethylamino, methylcarbonylamino and ethylcarbonylamino.

2. A compound according to claim 1, wherein such compound is 3-chloro-5-(4-tetrazol-1-yl-phenylthio)-1,2,4-oxadiazole of the formula

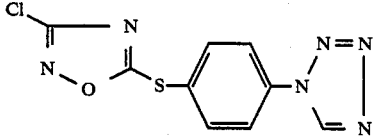

3. A compound according to claim 1, wherein such compound is 3-chloro-5-(4-acetamidophenylthio)-1,2,4-oxadiazole of the formula

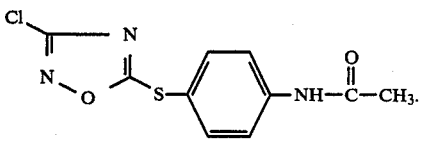

4. A compound according to claim 1, wherein such compound is 3-chloro-5-(4-phenylthiophenylthio)-1,2,4-oxadiazole of the formula

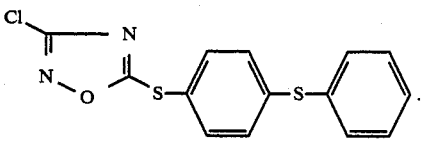

5. A compound according to claim 1, wherein such compound is 3-chloro-5-(quinolin-2-yl-thio)-1,2,4-oxadiazole of the formula

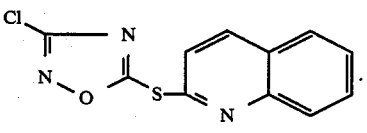

6. A fungicidal and bactericidal composition comprising a fungicidally and bactericidally effective amount of a compound according to claim 1 and a diluent.

7. A method of combating fungi, and bacteria which comprises applying to such fungi, bacteria or locus from which it is desired to exclude such fungi and bacteria a fungicidally and bactericidally effective amount of a compound according to claim 1.

8. The method according to claim 7, wherein such compound is
1,3-bis-(3-chloro-1,2,4-oxadiazol-5-yl-thio)-benzene,
3-chloro-5-(4-tetrazol-1-yl-phenylthio)-1,2,4-oxadiazole,
3-chloro-5-(4-acetamidophenylthio)-1,2,4-oxadiazole,
3-chloro-5-(4-phenylthiophenylthio)-1,2,4-oxadiazole or
3-chloro-5-(quinolin-2-yl-thio)-1,2,4-oxadiazole.

* * * * *